(12) United States Patent
Zeng et al.

(10) Patent No.: US 12,226,551 B2
(45) Date of Patent: Feb. 18, 2025

(54) DRUG RELEASE COATING COMPOSITIONS

(71) Applicant: BOSTON SCIENTIFIC SCIMED, INC., Maple Grove, MN (US)

(72) Inventors: Hongxia Zeng, Maple Grove, MN (US); Jonathan Pascal Chaky, Saint Paul, MN (US); Ming Dang, Plymouth, MN (US); Yen-Lane Chen, New Brighton, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 321 days.

(21) Appl. No.: 16/526,912

(22) Filed: Jul. 30, 2019

(65) Prior Publication Data
US 2020/0038559 A1 Feb. 6, 2020

Related U.S. Application Data (60) Provisional application No. 62/713,081, filed on Aug. 1, 2018.

(51) Int. Cl.
| | | |
|---|---|---|
| *A61L 31/10* | (2006.01) | |
| *A61K 31/436* | (2006.01) | |
| *A61K 47/34* | (2017.01) | |
| *A61K 47/38* | (2006.01) | |
| *A61L 29/08* | (2006.01) | |
| *A61L 29/16* | (2006.01) | |
| *A61L 31/16* | (2006.01) | |

(52) U.S. Cl.
CPC .......... *A61L 29/085* (2013.01); *A61K 31/436* (2013.01); *A61K 47/34* (2013.01); *A61K 47/38* (2013.01); *A61L 29/16* (2013.01); *A61L 2300/204* (2013.01); *A61L 2300/802* (2013.01); *A61L 2420/06* (2013.01)

(58) Field of Classification Search
None
See application file for complete search history.

(56) References Cited

U.S. PATENT DOCUMENTS

| | | |
|---|---|---|
| 7,121,558 B2 | 10/2006 | Cho |
| 7,232,486 B2 | 6/2007 | Keri et al. |
| 7,572,245 B2 | 8/2009 | Herweck et al. |
| 7,812,032 B2 | 10/2010 | Viswanath et al. |
| 8,211,455 B2 | 7/2012 | Schwarz |
| 8,480,620 B2 | 7/2013 | Stankus et al. |
| 8,669,360 B2 | 3/2014 | Zeng et al. |
| 8,951,595 B2 | 2/2015 | Stankus et al. |
| 9,381,270 B2 | 7/2016 | Makower et al. |
| 2003/0004565 A1* | 1/2003 | Harnek ................ A61L 17/005 623/1.15 |
| 2007/0038289 A1 | 2/2007 | Nishide et al. |
| 2007/0160641 A1* | 7/2007 | Jang ..................... A61L 29/085 424/423 |
| 2010/0272773 A1 | 10/2010 | Kangas et al. |
| 2010/0331816 A1 | 12/2010 | Dadino et al. |
| 2015/0031772 A1* | 1/2015 | Schallenberger ..... A61L 29/085 514/635 |
| 2015/0182732 A1 | 7/2015 | Zeng et al. |

FOREIGN PATENT DOCUMENTS

| | | |
|---|---|---|
| CN | 104623740 B | 5/2020 |
| DE | 102008043736 A1 | 5/2010 |
| JP | H09143059 A | 6/1997 |
| JP | 2005011796 A | 1/2005 |
| JP | 2010166936 A | 8/2010 |
| JP | 2011507665 A | 3/2011 |
| JP | 2015533305 A | 11/2015 |
| WO | 2009088726 A | 7/2009 |
| WO | 2010036604 A1 | 12/2010 |
| WO | 2011071630 A1 | 6/2011 |
| WO | 2013177211 A1 | 11/2013 |
| WO | 2014063111 A1 | 4/2014 |
| WO | 2015179515 A1 | 11/2015 |

OTHER PUBLICATIONS

Gad et al., AAPS PharmSciTech, 2008, 9(3), pp. 878-884 (Year: 2008).*
International Search Report and Written Opinion dated Oct. 31, 2019 for International Application No. PCT/US2019/044244.

* cited by examiner

*Primary Examiner* — Brian Gulledge
(74) *Attorney, Agent, or Firm* — Seager, Tufte & Wickhem, LLP (57) ABSTRACT

In one aspect, the present disclosure pertains to elutable coating compositions that comprise an excipient comprising a bio-degradable or bio-stable polymer selected from a poly(lactic-co-glycolic acid) (PLGA) or methyl cellulose (MCC), a binding agent; a therapeutic agent. In some embodiments, the elutable coating compositions further comprise a solvent, in which case such compositions may be, for example, applied to a substrate in the form of a layer and subsequently dried, thereby forming an elutable coating on the substrate.

14 Claims, 4 Drawing Sheets

DRUG RELEASE COATING COMPOSITIONS

CROSS-REFERENCE TO RELATED APPLICATIONS

This application claims the benefit of priority under 35 U.S.C. § 119 to U.S. Provisional Application Ser. No. 62/713,081, filed Aug. 1, 2018, the entirety of which is incorporated herein by reference.

FIELD

The present disclosure pertains to medical devices, and methods for manufacturing medical devices. More particularly, the present disclosure pertains to medical devices for therapeutic agent delivery.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices. For example, drug coated medical devices may allow for transfer of a therapeutic agent to a target region within the body. It may be desirable to provide coating compositions which safely and reliably increase drug transfer efficiency.

BRIEF SUMMARY

This disclosure provides design, material, manufacturing method, and use alternatives for medical devices.

In a first example, an elutable coating composition may comprise an excipient comprising a bio-degradable or bio-stable polymer selected from a poly(lactic-co-glycolic acid) (PLGA) or methyl cellulose (MCC), a binding agent, and a therapeutic agent.

Alternatively or additionally to any of the examples above, in another example, the binding agent may comprise ethyl cellulose.

Alternatively or additionally to any of the examples above, in another example, the excipient may comprise PLGA (50:50).

Alternatively or additionally to any of the examples above, in another example, the excipient may comprise PLGA (85:15).

Alternatively or additionally to any of the examples above, in another example, an intrinsic viscosity of the excipient may be in the range of about 0.1 deciliters/gram (dL/g) to about 0.8 dL/g.

Alternatively or additionally to any of the examples above, in another example, the excipient may comprise MCC having a viscosity in the range of about 10 centipoise (cp) to about 500 cp as a 2% solution in water.

Alternatively or additionally to any of the examples above, in another example, the excipient may comprise MCC having a viscosity in the range of about 300 centipoise (cp) to about 4,000 cp as a 2% solution in water.

Alternatively or additionally to any of the examples above, in another example, the therapeutic agent may comprise in the range of about 60 to about 90 weight percent of the coating composition.

Alternatively or additionally to any of the examples above, in another example, the excipient may comprise in the range of about 5 to about 40 weight percent of the coating composition.

Alternatively or additionally to any of the examples above, in another example, the binding agent may comprise in the range of about 5 to about 15 weight percent of the coating composition.

Alternatively or additionally to any of the examples above, in another example, the therapeutic agent may comprise about 60 to about 80 weight percent of the coating composition, the excipient may comprise about 10 to about 35 weight percent of the coating composition, and the binding agent may comprise about 5 to about 20 weight percent of the coating composition.

Alternatively or additionally to any of the examples above, in another example, the therapeutic agent may comprise everolimus.

In another example, a medical article may comprise a medical article substrate that is at least partially covered by a layer of the lubricous coating composition in accordance with any of the examples above.

Alternatively or additionally to any of the examples above, in another example, the medical article substrate may be an expandable balloon.

Alternatively or additionally to any of the examples above, in another example, the medical article substrate may be a stent.

In another example, an elutable coating composition may comprise an excipient comprising a poly(lactic-co-glycolic acid) (PLGA) having an intrinsic viscosity in the range of about 0.1 deciliters/gram (dL/g) to about 0.8 dL/g, a binding agent, and a therapeutic agent.

Alternatively or additionally to any of the examples above, in another example, the binding agent may comprise ethyl cellulose.

Alternatively or additionally to any of the examples above, in another example, the excipient may comprise PLGA (50:50).

Alternatively or additionally to any of the examples above, in another example, the excipient may comprise PLGA (85:15).

Alternatively or additionally to any of the examples above, in another example, the therapeutic agent may comprise in the range of about 60 to about 90 weight percent of the coating composition.

Alternatively or additionally to any of the examples above, in another example, the excipient may comprise in the range of about 5 to about 40 weight percent of the coating composition.

Alternatively or additionally to any of the examples above, in another example, the binding agent may comprise in the range of about 5 to about 15 weight percent of the coating composition.

Alternatively or additionally to any of the examples above, in another example, the therapeutic agent may comprise about 60 to about 80 weight percent of the coating composition, the excipient may comprise about 10 to about 35 weight percent of the coating composition, and the binding agent may comprise about 5 to about 20 weight percent of the coating composition.

Alternatively or additionally to any of the examples above, in another example, the therapeutic agent may comprise everolimus.

In another example, an elutable coating composition may comprise an excipient comprising a methyl cellulose (MCC), a binding agent, and a therapeutic agent.

Alternatively or additionally to any of the examples above, in another example, the binding agent may comprise ethyl cellulose.

Alternatively or additionally to any of the examples above, in another example, the MCC may have a viscosity in the range of about 10 centipoise (cp) to about 500 cp as a 2% solution in water.

Alternatively or additionally to any of the examples above, in another example, the MCC may have a viscosity in the range of about 300 centipoise (cp) to about 4,000 cp as a 2% solution in water.

Alternatively or additionally to any of the examples above, in another example, the therapeutic agent may comprise in the range of about 60 to about 90 weight percent of the coating composition.

Alternatively or additionally to any of the examples above, in another example, the excipient may comprise in the range of about 5 to about 40 weight percent of the coating composition.

Alternatively or additionally to any of the examples above, in another example, the binding agent may comprise in the range of about 5 to about 15 weight percent of the coating composition.

Alternatively or additionally to any of the examples above, in another example, the therapeutic agent may comprise about 60 to about 80 weight percent of the coating composition, the excipient may comprise about 10 to about 35 weight percent of the coating composition, and the binding agent may comprise about 5 to about 20 weight percent of the coating composition.

Alternatively or additionally to any of the examples above, in another example, the therapeutic agent may comprise everolimus.

In another example, a method of preparing an elutable coating composition may comprise mixing an excipient comprising poly(lactic-co-glycolic acid) (PLGA) or methyl cellulose (MCC), a binding agent comprising ethyl cellulose (ECC), and a therapeutic agent to form a mixture, dispersing the mixture in a first solvent to form a first suspension, adding the first suspension to a second solvent to form a second suspension, agitating the second suspension, and incubating the second suspension at room temperature for a length of time in the range of 24 to 72 hours.

Alternatively or additionally to any of the examples above, in another example, the excipient, binding agent, and therapeutic agent may be mixed at a weight ratio of about 1:1:8.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

The body includes various passageways such as blood vessels and body lumens. These passageways sometimes become occluded (for example, by a tumor or plaque). To widen an occluded body vessel, balloon catheters can be used, for example, in angioplasty. In some embodiments, a balloon catheter can include an inflatable and deflatable balloon carried by a long and narrow catheter body. The balloon can be initially folded around the catheter body to reduce the radial profile of the balloon catheter for easy insertion into the body. During use, the folded balloon can be delivered to a target location in the vessel, for example, a portion occluded by plaque, by threading the balloon catheter over a guide wire previously located in the vessel. The balloon is then inflated, for example, by introducing a fluid (such as a gas or a liquid) into the interior of the balloon. Inflating the balloon can radially expand the vessel so that the vessel can permit an increased rate of blood flow. After use, the balloon is typically deflated and withdrawn from the body. In some instances, it may be desirable to coat, layer, or otherwise apply a drug or therapeutic agent to an outer surface of the balloon to deliver and/or administer the drug or therapeutic agent to a lumen wall when the balloon is expanded. During deployment (e.g., expansion of the balloon), the coating including the drug or therapeutic agent may break apart into particulates. Some of the particulates may be partially deposited on the inner surface of the vessel. However, the efficiency of the transfer of the drug or therapeutic agent may be low. It may be desirable to provide a coating that can maintain high viscosity with sufficient particle bonding to resist drug loss when exposed to blood flow, which may improve drug transfer efficiency, but still maintain reasonable particulate profile (e.g., particulates shed within the body attributable to the coating are at a safe level). While the therapeutic coating described herein is discussed relative to balloons and balloon catheters, it is contemplated that the therapeutic coating can be applied to and/or used in conjunction with other medical devices, such as, but not limited to, stents, embolic filters, implantable devices, treatment devices, etc.

In some instances, drug coated balloons (DCB) have involved coating a blend of a drug and an excipient. Upon deployment of the balloon the coating may come off in a cascade of particulates. Some of the coating may be lost during tracking, some may be lost during deployment and a very small portion may be actually deposited on the artery (or other target location). The solid particulates on the artery wall may have one of several different potential outcomes. For example, some may be flushed from the artery wall into the blood stream. Those that remain in contact with the artery wall may slowly dissolve with some fraction dissolving into the blood stream and some fraction taken up by the vessel (e.g., the therapeutic dose). The coating compositions described herein may allow for high drug transfer efficiency, a safe particulate profile and sustained drug release.

Figure 1A:
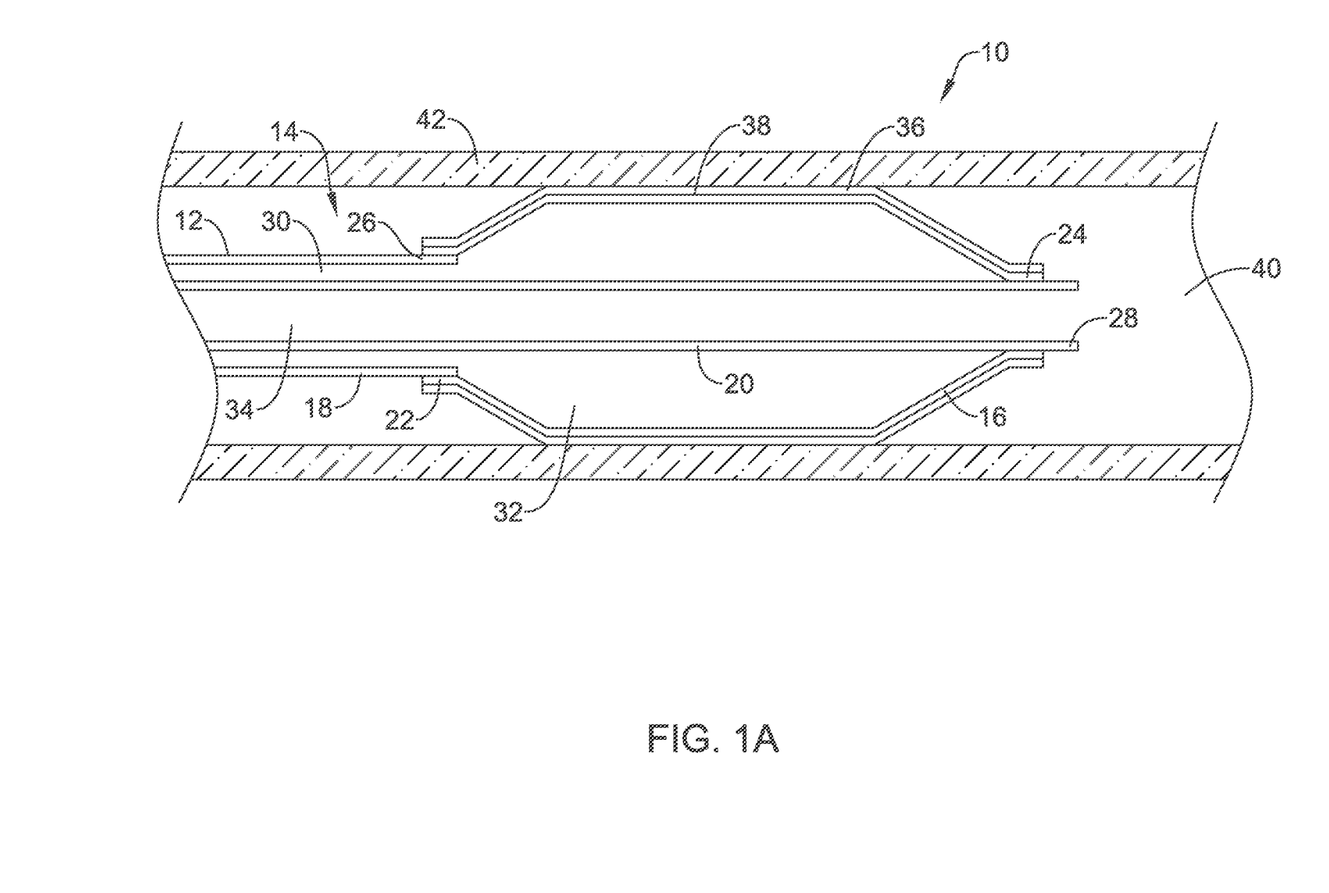
FIG. 1A is cross-sectional view of an illustrative medical device.

FIG. 1A is a cross-sectional side view of a distal end region of an example medical device 10 that, in this example, takes the form of a catheter, disposed in a body lumen 40. In at least some embodiments, the catheter 10 may be a balloon catheter. The catheter 10 may include an elongate catheter shaft 12 having a proximal end (not shown) and a distal end region 14. The catheter shaft 12 may extend proximally from the distal end region 14 to the proximal end which is configured to remain outside of a patient's body. Although not shown, the proximal end of the catheter shaft 12 may include a hub attached thereto for connecting other treatment devices or providing a port for facilitating other treatments. It is contemplated that the stiffness and size of the catheter shaft 12 may be modified to form a catheter 10 for use in various locations within the body. The catheter 10 may be configured to be advanced through a guide sheath, delivery sheath, or other guide means.

The catheter 10 may further include an inflatable balloon 16 affixed adjacent to the distal end region 14 of the catheter shaft 12. The size of the balloon 16 may vary based on where in the body it is used (e.g., along the coronary and/or peripheral vasculature, in a pulmonary vessel, along an airway, along another body lumen, or the like). The balloon 16 may have an outer diameter (in the inflated state) in the range of 1 millimeter (mm) to 26 mm, or about 2 to 10 mm, or about 2.5 to 8 mm. The balloon 16 may have a length in the range of 5 mm to 300 mm, or about 5 to 100 mm, or about 10 to 50 mm. The balloon 16 may have a wall thickness in the range of 10 micrometers (μm) to 100 μm, or about 10 to 75 μm, or about 10 to 50 μm.

The catheter shaft 12 may include an outer tubular member 18 and an inner tubular member 20. A proximal waist 22 of the balloon 16 may be secured to a distal end region 26 of the outer tubular member 18. A distal waist 24 of the balloon 16 may be secured to a distal end region 28 of the inner tubular member 20. The inner tubular member 20 may extend distally beyond the distal waist 24 of the balloon 16, although this is not required. In some instances, an annular inflation lumen 30 may be disposed between the outer tubular member 18 and the inner tubular member 20. The inflation lumen 30 may allow inflation fluid to pass from an inflation fluid source configured to remain outside the body to the interior region 32 of the balloon 16. The inner tubular member 20 may further define a lumen 34 through which a guidewire (not explicitly shown) may be passed in order to advance the catheter 10 to a predetermined position, although this is not required.

In some embodiments, an outer surface 38 of the balloon 16 may be coated with or otherwise include an elutable drug or coating 36. The coating 36 may include one or more polymers (e.g., an excipient), a binding agent, and a therapeutic agent or drug. The terms "therapeutic agents," "drugs," "bioactive agents," "pharmaceuticals," "pharmaceutically active agents", and other related terms may be used interchangeably herein and include genetic therapeutic agents, non-genetic therapeutic agents, and cells. Therapeutic agents may be used singly or in combination. A wide range of therapeutic agent loadings can be used in conjunction with the devices of the present invention, with the pharmaceutically effective amount being readily determined by those of ordinary skill in the art and ultimately depending, for example, upon the condition to be treated, the nature of the therapeutic agent itself, the tissue into which the dosage form is introduced, and so forth.

Some specific beneficial agents include anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

More specific drugs or therapeutic agents include paclitaxel, rapamycin, sirolimus, everolimus, tacrolimus, heparin, diclofenac, aspirin, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, and Serca 2 gene/protein, resiquimod, imiquimod (as well as other imidazoquinoline immune response modifiers), human apolioproteins (e.g., AI, AII, AIII, AIV, AV, etc.), vascular endothelial growth factors (e.g., VEGF-2), as well as derivatives of the forgoing, among many others.

Numerous additional therapeutic agents useful for the practice of the present invention may be selected from those described in commonly assigned U.S. Pat. No. 8,211,455, the entire disclosure of which is hereby incorporated by reference.

In one example, the drug coating 36 may include one or more excipients, one or more binding agents, and one or more therapeutic agents, such as, but not limited to everolimus. While the drug coating 36 described herein is discussed relative to everolimus, it is contemplated that other drugs or therapeutic agents may be used, as desired. Some illustrative excipients may include, but are not limited to poly(lactic-co-glycolic acid) (PLGA) or methyl cellulose (MCC). It is contemplated that other bio-degradable or bio-stable polymers may be used as desired. An illustrative, but non-limiting, binding agent may include ethyl cellulose. In some cases, the coating may comprise a mixture of poly(lactic-co-glycolic acid) (PLGA), ethyl cellulose (ECC), and everolimus. In another example, the coating may comprise a mixture of methyl cellulose (MCC), ECC, and everolimus. The weight percent (wt %) of the therapeutic agent in the elutable drug coating 36 may be in the range of about 50 to about 99% wt %, about 60 to about 95 wt %, or about 70 to about 90 wt %, or about 80 wt %. The weight percent of the excipient in the elutable drug coating 36 may be in the range of about 1 to about 45% wt %, about 5 to about 30 wt %, or about 10 wt %. The weight percent of the binding agent in the elutable drug coating 36 may be in the range of about 1 to about 20% wt %, about 5 to about 15 wt %, or about 10 wt %.

The properties of PLGA can be manipulated by changing the ratio of lactide to glycolide used during the polymerization process. The different forms may be identified by molar ratios of the monomers used. For example, PLGA 50:50 identifies a copolymer having a composition that is 50% lactic acid and 50% glycolic acid and PLGA 75:25 identifies a copolymer having a composition that is 75% lactic acid and 25% glycolic acid. PLGA can also be synthesized as a random copolymer or a block copolymer which may additionally be used to control the properties of the PLGA. In some instances, increasing the content of the glycolide may reduce the degradation time of the PLGA. An exception to this is PLGA 50:50 which may have the fastest degradation time. It is contemplated that release of a drug from a coating including a drug, a binding agent (e.g., ethyl cellulose), and PLGA may be modulated through manipulation of the lactic acid to glycolic acid ratio in the PLGA. For example, increasing the ratio of lactic acid in the PLGA may make the coating more hydrophobic (e.g., less water soluble) which may slow down the PLGA degradation time to modulate release of the therapeutic agent. It is further contemplated that increasing the molecular weight of the PLGA may increase the viscosity of the coating in situ as well as increasing the time it takes for the PLGA to dissolve which may help the therapeutic agent remain on the vessel wall for longer periods of time. Increasing the viscosity and the time to dissolve may increase the contact time of the coating with the vessel or target region thus allowing more drug to be absorbed into the body at the target region. Examples of PLGA materials useful in the present disclosure include PLGA (50:50) DL 2A, PLGA (85:15) DL 4A, and PLGA (85:15) DL high IV, all available from Evonik Industries AG (Essen, Germany). Suitable PLGA materials may have an intrinsic viscosity in the range of about 0.1 deciliters/gram (dL/g) to about 0.8 dL/g. It is further contemplated that PLGA materials having an intrinsic viscosity of less than 0.1 dL/g or greater than 0.8 dL/g may also be used.

The properties of the coating 36 may be also be manipulated when methyl cellulose is used as the excipient. In some cases, the properties of methyl cellulose can be changed depending on the number of hydroxyl groups that are replaced by methoxide during the synthesis and/or on the average length of the polymer backbone. For example, the viscosity of an aqueous solution of the methyl cellulose may be proportional to the molecular weight or chain length of the particular formulation. As described above, increasing the viscosity and the time to dissolve may increase the contact time of the coating with the vessel or target region thus allowing more drug to be absorbed into the body at the target region. Examples of MCC materials useful in the present disclosure include Methocel® A15 LV, Methocel® A4C Premium, and Methocel® A4M (HV), all available from The Dow Chemical Company, Midland, MI Suitable MCC materials may have a viscosity (based on a 2% solution of MCC in water) in the range of 10 centipoise (cp) to about 4,000 (cp), or about 10 cp to about 500 cp, or about 300 cp to about 4,000 cp. It is further contemplated that MCC materials having a viscosity of less than 10 cp or greater than 4,000 cp may also be used.

The binding agent may be used to bundle the drug particles together (e.g., through increasing cohesive force). Binding the drug particles may allow the drug to remain at the target region for a longer period of time (e.g., reducing the number of blood particles that get flushed from the target region by a flowing body fluid, such as blood). In some cases, ethyl cellulose (ECC) may be used as the binding agent, however other binding agents may be used, such as, but not limited to, starch, xanthan gum, guar gum, povidone, etc.

In preparing liquid coating composition for application to the balloon 16, the drug (such as, but not limited to, everolimus) may first be converted from an amorphous form to a crystalline form. Briefly, a slurry of the amorphous drug and a solvent may be formed and allowed to age. Illustrative methods for converting amorphous macrolide drugs to crystalline everolimus is described in commonly assigned U.S. Pat. No. 8,669,360, the entire disclosure of which is hereby incorporated by reference. However, in some instances, the everolimus may be converted from an amorphous form to a crystalline form while the liquid coating suspension is being prepared. The liquid suspension may be used to facilitate crystalline grown with a narrower size distribution The drug, excipient, and binding agent may then be added to a first solvent, such as, but not limited to, ethyl acetate, to form a first solution or suspension. The first suspension (e.g., the drug, excipient, binding agent, and first solvent) may then be dispensed into a second solvent, such as, but not limited to, heptane, to form a second suspension including the solvents and the coating composition. In some cases, the first suspension may be added dropwise (e.g., from a pipette or dropper) into the second solvent. It is contemplated that the first and second solvents may be used in various quantities. For example, the ratio of the first solvent to the second solvent in the second suspension may range from about 1:10 to about 10:1.

The second suspension may then be agitated (e.g., shaken or stirred) and allowed to incubate. In some examples, the second suspension may incubate at 29° C. for approximately 72 hours. The incubation period may allow an amorphous drug to crystallize. The second suspension may be applied to the medical device (e.g., the balloon 16) by any method known in the art including, but not limited to, spraying, dipping, rolling, pipetting, painting (e.g., brush painting, sponge painting, etc.), and so forth. The second suspension may then be allowed to dry, by evaporation of the solvent to form the drug coating 36. In some instances, the balloon 16 may be allowed to dry at ambient conditions overnight. However, in some instances, the balloon 16 may be dried at elevated temperatures (e.g., above room temperature). In the dried form, the coating 36 may include about 50 weight percent (wt %) to about 90 wt % of the therapeutic agent, about 5 wt % to about 30 wt % of the excipient, and about 5 wt % to about 15 wt % of the binding agent. The therapeutic agent, excipient, and binding agent may have the same or similar weight ratio relative to one another in the suspension form as in the dry coating form. In some instances, some bio-degradable or bio-stable polymers may form microspheres. The dried coating may be analyzed (using, for example, differential scanning calorimetry or x-ray diffraction) to determine the percentage of crystallinity. In some cases, the dried coating may have in the range of about 60-90% of the dried coating in crystalline form.

In some embodiments the dried coating 36 may have a thickness on the balloon 16 in the range of from 0.1 micrometers or less to 20 micrometers or more (e.g., from 0.1 to 0.2 to 0.5 to 1 to 2 to 5 to 10 to 20 micrometers), or about 0.1 to about 5 micrometers. The coating thickness may be affected by the percent solids in the second suspension and the technique of application, among other factors. Multiple coatings may be applied to achieve a desired coating thickness.

In some embodiments, the elutable drug coating 36 may cover the entire surface area 38 of the balloon 16. In other embodiments, the elutable drug coating 36 may cover a portion of the surface area of the balloon 16. For example, the elutable drug coating 36 may cover 90% or less (e.g., about 80% or less, about 70% or less, about 60% or less, about 50% or less, about 40% or less, about 30% or less, about 20% or less, or about 10% or less) and/or about 10% or more (e.g., about 20% or more, about 30% or more, about 40% or more, about 50% or more, about 60% or more, about 70% or more, 80% or more, or about 90% or more) of the balloon's outer surface 38.

In some embodiments, the catheter 10 may be advanced through a lumen 40 having a lumen wall 42, with or without a guidewire, or other guide means. When the balloon 16 is positioned adjacent to the desired treatment region, the balloon 16 may be expanded to bring the elutable drug coating 36 into contact with the lumen wall 42. The drug coating 36 may elute a therapeutic agent, such as, but not limited to, everolimus microparticles to the body lumen wall 42. The balloon 16 may remain inflated for a desired amount of time is sufficient to transfer the coating 36 from the balloon 16 to the wall 42.

As described herein, the excipient in the coating 36 may be water soluble. Once the coating 36 has been transferred to the wall 42, the coating 36 may begin to dissolve or be washed away by the flow of blood. An excipient that has a higher viscosity as it hydrates may have a longer contact time with the vessel wall 42 (e.g., may wash away less easily) thus allowing for an increased amount of drug transfer from the coating 36 to the lumen wall 42. In other words, as the intrinsic viscosity of the excipient increases, the ability of the coating 36 to remain in contact with the vessel wall 42 may also increase. As used herein, the intrinsic viscosity of the excipient refers to a measure of the solute's (e.g., the excipient's) contribution to the viscosity of a solution.

Figure 1B:
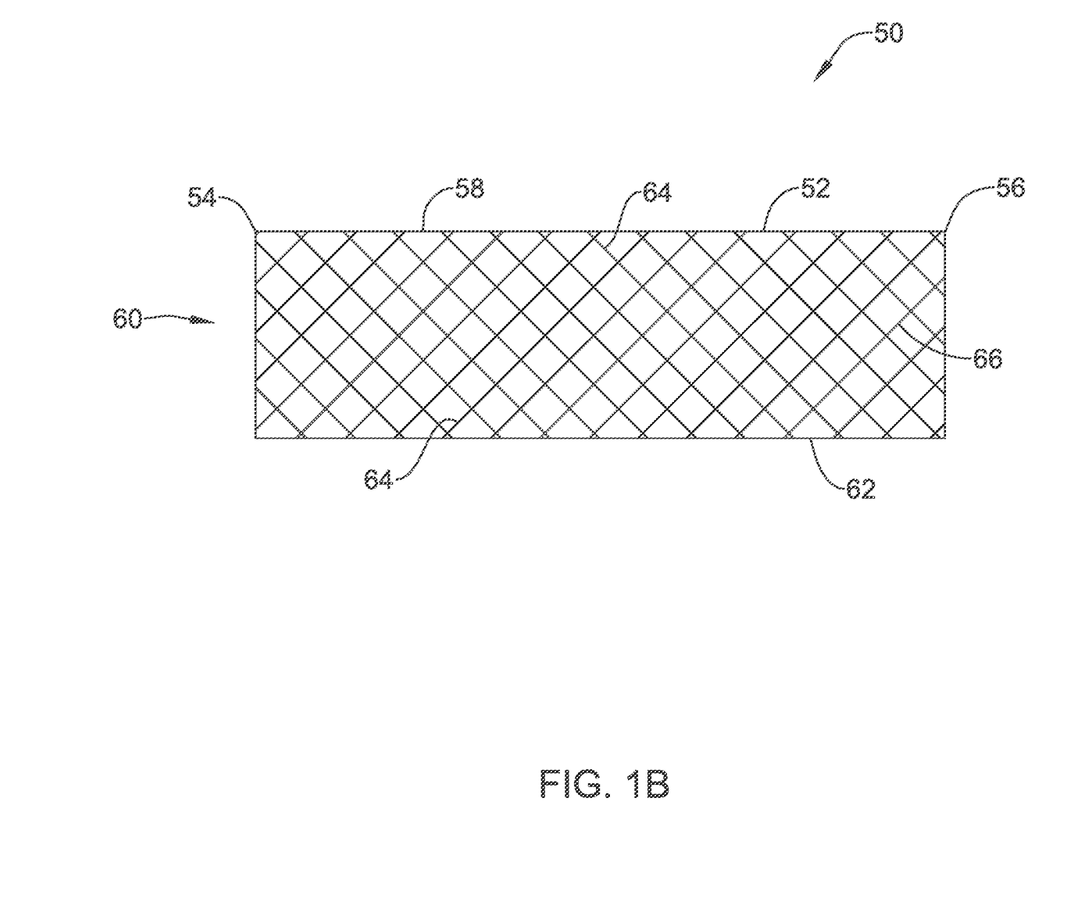
FIG. 1B is a side view of an illustrative endoluminal implant.

FIG. 1B illustrates a side view of an illustrative endoluminal implant 50, such as, but not limited to, a stent. In some instances, the stent 50 may be formed from an elongated tubular member 52. While the stent 50 is described as generally tubular, it is contemplated that the stent 50 may take any cross-sectional shape desired. The stent 50 may have a first, or proximal, end 54 and a second, or distal, end 56. The stent 50 may include a lumen 60 extending from a first opening adjacent the first end 54 to a second opening adjacent to the second end 56 to allow for the passage of food, fluids, etc. In some embodiments, an outer surface 62 of the stent 50 may be coated with or otherwise include an elutable drug or coating 66. The coating 66 may be similar in form and function to the elutable drug coating 36 described herein. Alternatively, or additionally, the coating 66 may be coated onto an inner surface of the stent 50.

In some embodiments, the elutable drug coating 66 may cover the entire surface area of the stent 50. In other embodiments, the elutable drug coating 66 may cover a portion of the surface area of the stent 50. For example, the elutable drug coating 66 may cover 90% or less (e.g., about 80% or less, about 70% or less, about 60% or less, about 50% or less, about 40% or less, about 30% or less, about 20% or less, or about 10% or less) and/or about 10% or more (e.g., about 20% or more, about 30% or more, about 40% or more, about 50% or more, about 60% or more, about 70% or more, 80% or more, or 90% or more) of the stent 50.

The stent 50 may be expandable from a first collapsed configuration (not explicitly shown) to a second expanded configuration. The stent 50 may be structured to extend across is a stricture and to apply a radially outward pressure to the stricture in a lumen to open the lumen and allow for the passage of foods, fluids, air, etc.

The stent 50 may have a woven structure, fabricated from a number of filaments or struts 64. In some embodiments, the stent 50 may be braided with one filament. In other embodiments, the stent 50 may be braided with several filaments, as is found, for example, in the WallFlex®, WALLSTENT®, and Polyflex® stents, made and distributed by Boston Scientific, Corporation. In another embodiment, the stent 50 may be knitted, such as the Ultraflex™ stents made by Boston Scientific, Corporation. In yet another embodiment, the stent 50 may be of a knotted type, such the Precision Colonic™ stents made by Boston Scientific, Corporation. In still another embodiment, the stent 50 may be a laser cut tubular member, such as the EPIC™ stents made by Boston Scientific, Corporation. A laser cut tubular member may have an open and/or closed cell geometry including one or more interconnected filaments. In some instances, an inner and/or outer surface of the stent 50 may be entirely, substantially or partially, covered with a polymeric covering or coating. For example, a covering or coating which may help reduce food impaction and/or tumor or tissue ingrowth.

The disclosure may be further clarified by reference to the following Examples, which serve to exemplify some of the embodiments, and not to limit the disclosure.

Example 1

Three coating compositions were prepared using the bio-degradable polymer poly(lactic-co-glycolic acid) (PLGA). Each coating composition used a different grade of PLGA with different viscosities. The first coating composition was prepared with a PLGA (50:50) having an intrinsic viscosity (IV) of 0.16 deciliters per gram (dL/g). The second coating composition was prepared with a PLGA (85:15) having an intrinsic viscosity of 0.41 to dL/g. The third coating composition was prepared with a PLGA (85:15) having an intrinsic viscosity of 0.75 dL/g. Each coating compositions were individually prepared by first mixing crystalline everolimus, ethyl cellulose (ECC), and PLGA at a weight ratio of 8:1:1 (everolimus:ECC:PLGA) to form a first mixture. Each composition was then dissolved individually in ethyl acetate at a weight ratio of 8:1:1:90 (everolimus:ECC:PLGA:ethyl is acetate) to form a first suspension. The first suspension was then dispersed dropwise into heptane at a weight ratio of 1:5 ethyl acetate to heptane to form a second suspension. The second suspension was then agitated (e.g., shaken or stirred) and allowed to incubate at 29° C. for approximately 72 hours. Each liquid coating composition was then coated onto two different balloons such that six balloons were coated with a PLGA containing composition. The balloons were allowed to dry at ambient conditions overnight. Two balloons were also coated with a coating composition having only crystalline everolimus. The dried coating compositions are listed in Table 1 below.

TABLE 1

Coating Compositions

| Control | Composition 1 | Composition 2 | Composition 3 |
|---|---|---|---|
| Crystalline Everolimus (100 wt %) | Crystalline Everolimus (80 wt %) PLGA (50:50) with an IV = 0.16 dL/g (10 wt %) Ethyl Cellulose (10 wt %) | Crystalline Everolimus (80 wt %) PLGA (85:15) with an IV = 0.41 dL/g (10 wt %) Ethyl Cellulose (10 wt %) | Crystalline Everolimus (80 wt %) PLGA (85:15) with an IV = 0.75 dL/g (10 wt %) Ethyl Cellulose (10 wt %) |

Figure 2:
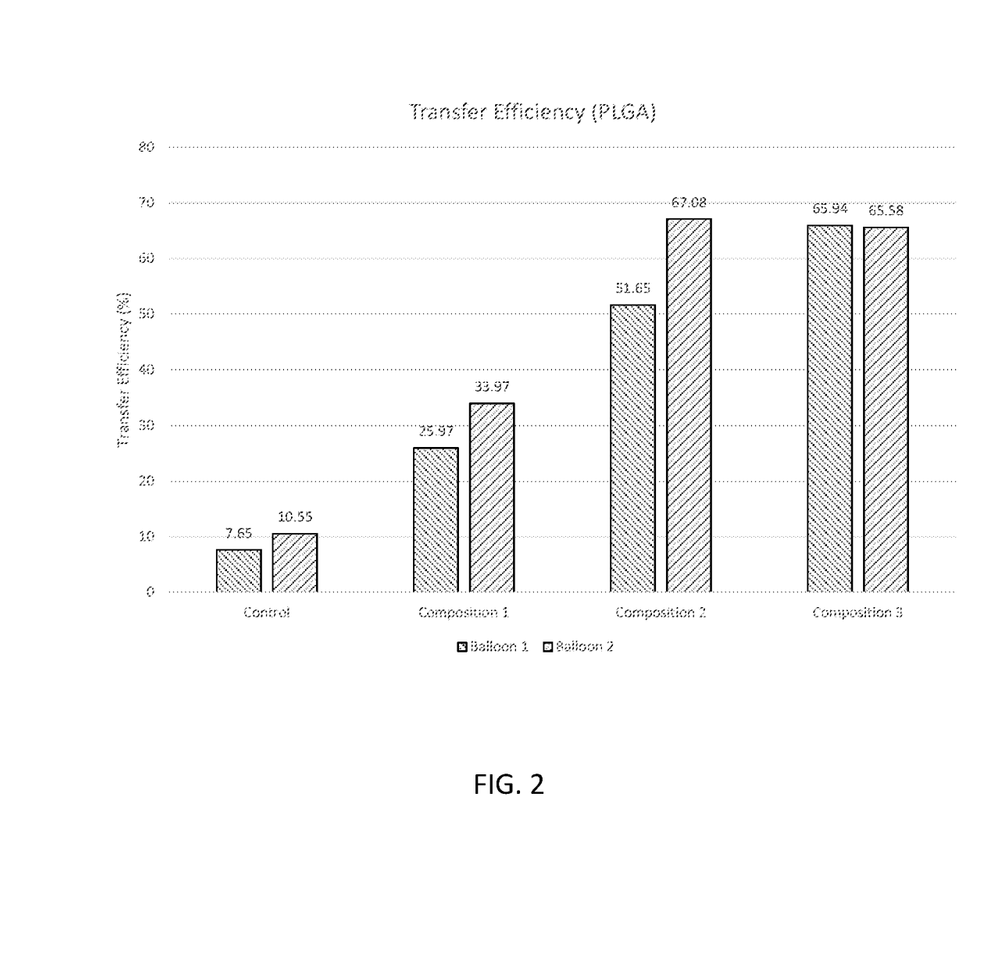
FIG. 2 is graph of transfer efficiency of a drug coating composition including a bio-degradable polymer.

The coated balloons were individually advanced through a plastic tube being flushed with water to simulate blood flow. At a target location within the plastic tube, the balloon was expanded to simulate delivery of the therapeutic drug within the body. The balloon was then deflated and removed from the tube. The water used to flush the plastic tube was collected and analyzed to determine how much of the therapeutic agent (e.g., everolimus) was lost in the simulated blood flow. After removal of the balloon, the plastic tube was also analyzed to determine how much of the therapeutic agent was transferred to the tube. Similarly, the balloon was analyzed to determine how much of the therapeutic drug remained on the balloon. The transfer efficiency (e.g., of drug to the tube wall) was then determined using the following equation:

$$\text{Transfer Efficiency} = \frac{\text{drug on tube}}{\text{total drug}} * 100$$

where the total drug is the sum of the drug in the water used for flushing, the drug on the tube, and the drug remaining on the balloon. The results are illustrated in FIG. 2 which illustrates a graph of drug transfer efficiency using a biodegradable polymer. As can be seen, the additional of PLGA and ECC improves transfer efficiency compared to a coating having only everolimus. The drug transfer efficiency also increases as the intrinsic viscosity of the PLGA increases.

The water used to flush the tube (e.g., the simulated blood) was also analyzed to determine the particulate burden for the coating compositions. The quantity of particulates was determined for three particle sizes (10 micron, 25 micron, and 50 micron) using light obscuration and normalized by the size of the balloon. The particulates for each coating and each size range are summarized in the table below:

TABLE 2

Particulate Comparison

| | Control | Composition 1 | Composition 2 | Composition 3 |
|---|---|---|---|---|
| | | 10 micron | | |
| Balloon 1 | 3110 | 4004 | 4762 | 3435 |
| Balloon 2 | 1521 | 3176 | 5153 | 2625 |

TABLE 2-continued

Particulate Comparison

| | Control | Composition 1 | Composition 2 | Composition 3 |
|---|---|---|---|---|
| | | 25 micron | | |
| Balloon 1 | 144 | 4 | 15 | 22 |
| Balloon 2 | 97 | 2 | 11 | 12 |
| | | 50 micron | | |
| Balloon 1 | 27 | 0 | 7 | 15 |
| Balloon 2 | 20 | 0 | 5 | 6 |

While the particulate burden for the 10 micron size range has increased with the addition of the PLGA and ECC, the particulate burden for the 25 and 50 micron ranges has decreased. However, the particulate burden for the 10 micron size range for compositions including PLGA and ECC are still within acceptable ranges. It should be noted that having fewer large particulates is very desirable, which is accomplished with the compositions including PLGA and ECC.

Example 2

Three coating compositions were prepared using the bio-stable polymer methyl cellulose (MCC). Each coating composition used a different grade of MCC with different viscosities. The first coating composition was prepared with an MCC having a viscosity of 15 centipoise (cp). The second coating composition was prepared with an MCC having a viscosity of 400 cp. The third coating composition was prepared with an MCC having a viscosity of 3893 cp. The viscosity of the different grades of MCC was based on a 2% solution of MCC in water. Each coating compositions were individually prepared by first mixing crystalline everolimus, ethyl cellulose (ECC), and MCC at a weight ratio of 8:1:1 (everolimus:ECC:MCC) to form a first mixture. Each composition was then dissolved individually in ethyl acetate at a weight ratio of 8:1:1:90 (everolimus:ECC:PLGA:ethyl acetate) to form a first suspension. The first suspension was then dispersed dropwise into heptane at a weight ratio of 1:5 ethyl acetate to heptane to form a second suspension. The second suspension was then agitated (e.g., shaken or stirred) and allowed to incubate at 29° C. for approximately 24-72 hours. Each liquid coating composition was then coated onto two different balloons such that six balloons were coated with an MCC containing composition. The balloons were allowed to dry at ambient conditions overnight. Two balloons were also coated with a coating composition having only crystalline everolimus. The dried coating compositions are listed in Table 3 below.

TABLE 3

Coating Compositions

| Control | Composition 1 | Composition 2 | Composition 3 |
|---|---|---|---|
| Crystalline Everolimus (100 wt %) | Crystalline Everolimus (80 wt %) MCC with a viscosity of 15 cp (2% in water) (10 wt %) Ethyl Cellulose (10 wt %) | Crystalline Everolimus (80 wt %) MCC with a viscosity of 400 cp (2% in water) (10 wt %) Ethyl Cellulose (10 wt %) | Crystalline Everolimus (80 wt %) MCC with a viscosity of 3893 cp (2% in water) (10 wt %) Ethyl Cellulose (10 wt %) |

Figure 3:
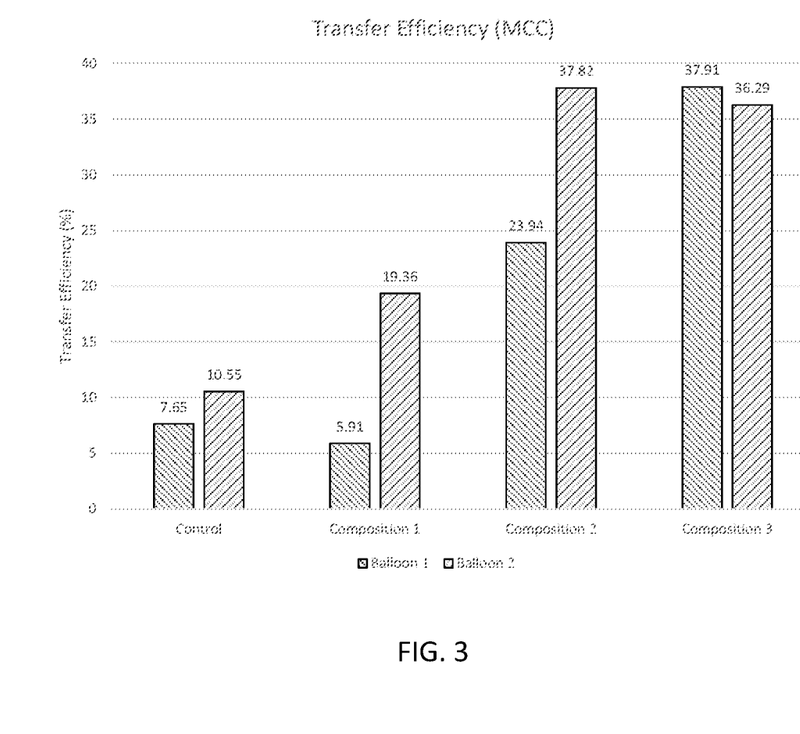
FIG. 3 is graph of transfer efficiency of a drug coating composition including a bio-stable polymer.

The coated balloons were individually advanced through a plastic tube being flushed with water to simulate blood flow. At a target location within the plastic tube, the balloon was expanded to simulate delivery of the therapeutic drug within the body. The balloon was then deflated and removed from the tube. The water used to flush the plastic tube was collected and analyzed to determine how much of the therapeutic agent (e.g., everolimus) was lost in the simulated blood flow. After removal of the balloon, the plastic tube was also analyzed to determine how much of the therapeutic agent was transferred to the tube. Similarly, the balloon was analyzed to determine how much of the therapeutic drug remained on the balloon. The transfer efficiency (e.g., of drug to the tube wall) was then determined using the following equation:

$$\text{Transfer Efficiency} = \frac{\text{drug on tube}}{\text{total drug}} * 100$$

where the total drug is the sum of the drug in the water used for flushing, the drug on the tube, and the drug remaining on the balloon. The results are illustrated in FIG. 3 which illustrates a graph of drug transfer efficiency using a biostable polymer. As can be seen, the additional of MCC and ECC improves transfer efficiency compared to a coating having only everolimus. The drug transfer efficiency also increases as the viscosity of the MCC increases. The variation between the samples was also reduced at higher viscosities.

The water used to flush the tube (e.g., the simulated blood) was also analyzed to determine the particulate burden for the coating compositions. The quantity of particulates was determined for three particle sizes (10 micron, 25 micron, and 50 micron) using light obscuration and normalized by the size of the balloon. The particulates for each coating and each size range are summarized in the table below:

TABLE 4

Particulate Comparison

|  | Control | Composition 1 | Composition 2 | Composition 3 |
|---|---|---|---|---|
| 10 micron | | | | |
| Balloon 1 | 3110 | 18310 | 13805 | 7586 |
| Balloon 2 | 1521 | 15292 | 6544 | 8725 |
| 25 micron | | | | |
| Balloon 1 | 144 | 27 | 20 | 18 |
| Balloon 2 | 97 | 22 | 5 | 21 |
| 50 micron | | | | |
| Balloon 1 | 27 | 12 | 10 | 10 |
| Balloon 2 | 20 | 10 | 2 | 11 |

While the particulate burden for the 10 micron size range has increased with the addition of the MCC and ECC, the particulate burden for the 25 and 50 micron ranges has decreased. However, the particulate burden for the 10 micron size range for compositions including MCC and ECC are still within acceptable ranges. It should be noted that having fewer large particulates is very desirable, which is accomplished with the compositions including MCC and ECC.

The materials that can be used for the various components of catheter 10 (and/or other devices disclosed herein) and the various tubular members disclosed herein may include those commonly associated with medical devices. For simplicity purposes, the following discussion makes reference to catheter 10. However, this is not intended to limit the devices and methods described herein, as the discussion may be applied to other similar medical devices and/or components of medical devices disclosed herein.

Catheter 10 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium is alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of catheter 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of catheter 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of catheter 10 to achieve the is same result.

In some embodiments, a degree of Magnetic Resonance Imaging (Mill) compatibility is imparted into catheter 10. For example, catheter 10, or portions thereof, may be made of a material that does not substantially distort the image and create substantial artifacts (i.e., gaps in the image). Certain ferromagnetic materials, for example, may not be suitable because they may create artifacts in an Mill image. Catheter 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An elutable coating composition comprising:
an excipient comprising a poly(lactic-co-glycolic acid) (PLGA) having an intrinsic viscosity in the range of about 0.1 deciliters/gram (dL/g) to about 0.8 dL/g;
a binding agent comprising ethyl cellulose; and
a therapeutic agent;
wherein the elutable coating composition maintains a high viscosity with sufficient particle bonding to resist drug loss when exposed to blood flow and reduces the particulate burden in the 25 to 50 micron ranges,
wherein the excipient comprises in the range of about 5 to 40 weight percent of the coating composition.

2. The elutable coating composition of claim 1, wherein the excipient comprises PLGA (50:50).

3. The elutable coating composition of claim 1, wherein the excipient comprises PLGA (85:15).

4. The elutable coating composition of claim 1, wherein the therapeutic agent comprises in the range of about 60 to about 90 weight percent of the coating composition.

5. The elutable coating composition of claim 1, wherein the binding agent comprises in the range of about 5 to about 15 weight percent of the coating composition.

6. The elutable coating composition of claim 1, wherein the therapeutic agent comprises everolimus.

7. An elutable coating composition comprising:
an excipient comprising a poly(lactic-co-glycolic acid) (PLGA) having an intrinsic viscosity in the range of about 0.1 deciliters/gram (dL/g) to about 0.8 dL/g;
a binding agent comprising ethyl cellulose; and
a therapeutic agent;
wherein the elutable coating composition maintains a high viscosity with sufficient particle bonding to resist drug loss when exposed to blood flow and reduces the particulate burden in the 25 to 50 micron ranges,
wherein the therapeutic agent comprises about 60 to about 80 weight percent of the coating composition, the excipient comprises about 10 to about 35 weight percent of the coating composition, and the binding agent comprises about 5 to about 20 weight percent of the coating composition.

8. An elutable coating composition comprising:
an excipient comprising a poly(lactic-co-glycolic acid) (PLGA) having an intrinsic viscosity in the range of about 0.1 deciliters/gram (dL/g) to about 0.8 dL/g;
a binding agent; and
a therapeutic agent;
wherein the excipient comprises in the range of about 5 to 40 weight percent of the coating composition,
wherein the elutable coating composition maintains a high viscosity with sufficient particle bonding to resist drug loss when exposed to blood flow and reduces the particulate burden in the 25 to 50 micron ranges.

9. The elutable coating composition of claim 8, wherein the excipient comprises PLGA (50:50).

10. The elutable coating composition of claim 8, wherein the excipient comprises PLGA (85:15).

11. The elutable coating composition of claim 8, wherein the therapeutic agent comprises in the range of about 60 to about 90 weight percent of the coating composition.

12. The elutable coating composition of claim 8, wherein the binding agent comprises in the range of about 5 to about 15 weight percent of the coating composition.

13. The elutable coating composition of claim 8, wherein the therapeutic agent comprises about 60 to about 80 weight percent of the coating composition, the excipient comprises about 10 to about 35 weight percent of the coating composition, and the binding agent comprises about 5 to about 20 weight percent of the coating composition.

14. The elutable coating composition of claim 8, wherein the therapeutic agent comprises everolimus.

* * * * *